US00PP28378P3

(12) United States Plant Patent
Wain

(10) Patent No.: US PP28,378 P3
(45) Date of Patent: Sep. 12, 2017

(54) ***CHRYSANTHEMUM* PLANT NAMED 'FIDCSUNWHI'**

(50) Latin Name: *Chrysanthemum×morifolium*
Varietal Denomination: Fidcsunwhi

(71) Applicant: Peter Wain, Locks Heath (GB)

(72) Inventor: Peter Wain, Locks Heath (GB)

(73) Assignee: Dümmer Group B.V., De Lier (NL)

( * ) Notice: Subject to any disclaimer, the term of this patent is extended or adjusted under 35 U.S.C. 154(b) by 105 days.

(21) Appl. No.: 14/757,060

(22) Filed: Nov. 11, 2015

(65) Prior Publication Data

US 2017/0135270 P1 May 11, 2017

(51) Int. Cl.
*A01H 5/02* (2006.01)

(52) U.S. Cl.
USPC ..... Plt./288

(58) Field of Classification Search
USPC ..... Plt./288
See application file for complete search history.

*Primary Examiner* — Anne Grunberg
(74) *Attorney, Agent, or Firm* — C. A. Whealy

(57) ABSTRACT

A new and distinct cultivar of *Chrysanthemum* plant named 'Fidcsunwhi', characterized by its upright to outwardly spreading and uniformly mounded plant habit; relatively compact growth habit; freely branching habit; dense and full plant form; uniform and freely flowering habit; medium-size decorative-type inflorescences with white-colored ray florets; early to mid-season flowering habit; and good garden performance.

1 Drawing Sheet

Botanical designation: *Chrysanthemum×morifolium.*
Cultivar denomination: 'FIDCSUNWHI'.

BACKGROUND OF THE INVENTION

The present invention relates to a new and distinct *Chrysanthemum* plant, botanically known as *Chrysanthemum×morifolium*, commercially grown as a garden *Chrysanthemum* plant and hereinafter referred to by the name 'Fidcsunwhi'.

The new *Chrysanthemum* plant is a product of a planned breeding program conducted by the Inventor in Fareham, Hampshire, United Kingdom. The objective of the breeding program is to create new early to mid-season flowering garden *Chrysanthemum* plants with numerous attractive inflorescences.

The new *Chrysanthemum* plant originated from a cross-pollination made in January, 2011 by the Inventor in Fareham, Hampshire, United Kingdom of a proprietary selection of *Chrysanthemum×morifolium* identified as code number 92122, not patented, as the female, or seed, parent with a proprietary selection of *Chrysanthemum×morifolium* identified as code number 83277, not patented, as the male, or pollen, parent. The new *Chrysanthemum* plant was discovered and selected by the Inventor as a single flowering plant from within the progeny of the stated cross-pollination in a controlled greenhouse environment in Fareham, Hampshire, United Kingdom in September, 2011.

Asexual reproduction of the new *Chrysanthemum* plant by terminal vegetative cuttings was first conducted in Fareham, Hampshire, United Kingdom in December, 2011. Asexual reproduction by terminal vegetative cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Fidcsunwhi'. These characteristics in combination distinguish 'Fidcsunwhi' as a new and distinct *Chrysanthemum* plant:

1. Upright to outwardly spreading and uniformly mounded plant habit.
2. Relatively compact growth habit.
3. Freely branching habit; dense and full plant form.
4. Uniform and freely flowering habit.
5. Medium-size decorative-type inflorescences with white- colored ray florets.
6. Early to mid-season flowering habit, grown under natural season conditions, plants flower in late August to early September in the United Kingdom.
7. Good garden performance.

Plants of the new *Chrysanthemum* can be compared to plants of the female parent selection. Plants of the new *Chrysanthemum* differ from plants of the female parent selection in the following characteristics:

1. Grown under natural season conditions, plants of the new *Chrysanthemum* flower earlier than plants of the female parent selection.
2. Plants of the new *Chrysanthemum* have larger inflorescences than plants of the female parent selection.

Plants of the new *Chrysanthemum* can be compared to plants of the male parent selection. Plants of the new *Chrysanthemum* differ from plants of the male parent selection in the following characteristics:

1. Plants of the new *Chrysanthemum* are more compact than and not as vigorous as plants of the male parent selection.

2. Plants of the new *Chrysanthemum* and the male parent selection differ in ray floret color as plants of the male parent selection have inflorescences with yellow-colored ray florets.

Plants of the new *Chrysanthemum* can be compared to plants of *Chrysanthemum×morifolium* 'Jasoda White', disclosed in U.S. Plant Pat. No. 21,884. In side-by-side comparisons conducted in Fareham, Hampshire, United Kingdom, plants of the new *Chrysanthemum* differed from plants of 'Jasoda White' in the following characteristics:

1. Grown under natural season conditions, plants of the new *Chrysanthemum* flowered about one month earlier than plants of 'Jasoda White'.
2. Plants of the new *Chrysanthemum* had larger inflorescences than plants of 'Jasoda White'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant.

The photograph is a side perspective view of a typical flowering plant of 'Fidcsunwhi' grown in a 19-cm container.

DETAILED BOTANICAL DESCRIPTION

The aforementioned photograph and following observations and measurements describe plants grown during the winter in 19-cm containers in a glass-covered greenhouse in Fareham, Hampshire, United Kingdom and under cultural practices typical of commercial garden *Chrysanthemum* production. During the production of the plants, day and night temperatures ranged from 17° C. to 21° C. and light levels averaged 6,000 lux. Plants were grown under long day/short night conditions for eight weeks (including propagation period) and then grown under short day/long night conditions to induce inflorescence initiation and development. Plants were 14 weeks old when the photograph and detailed description were taken. In the following description, color references are made to The Royal Horticultural Society Colour Chart, Fifth Edition, except where general terms of ordinary dictionary significance are used.

Botanical classification: *Chrysanthemum×morifolium* 'Fidcsunwhi'.

Parentage:

*Female, or seed, parent.*—Proprietary selection of *Chrysanthemum×morifolium* identified as code number 92122, not patented.

*Male, or pollen, parent.*—Proprietary selection of *Chrysanthemum×morifolium* identified as code number 83277, not patented.

Propagation:

*Type.*—Terminal vegetative cuttings.

*Time to initiate roots, summer.*—About ten days at temperatures about 21° C.

*Time to initiate roots, winter.*—About twelve days at temperatures about 21° C.

*Time to produce a rooted young plant, summer.*—About three weeks at temperatures about 21° C.

*Time to produce a rooted young plant, winter.*—About four weeks at temperatures about 21° C.

*Root description.*—Fine, fibrous; typically light brown in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Herbaceous decorative-type garden *Chrysanthemum*; stems upright to outwardly spreading giving a uniformly mounded appearance to the plant; numerous lateral branches and relatively short internodes, dense and full plant form; relatively compact growth habit.

*Plant height.*—About 15 cm.

*Plant width.*—About 27 cm.

*Main stem diameter.*—About 5 mm.

*Branching habit.*—Freely branching habit; about nine lateral branches develop after removal of terminal apex (pinching).

*Lateral branches.*—Length: About 10 cm. Diameter: About 3 mm. Internode length: About 1.5 cm. Strength: Moderately strong. Aspect: About 60° from the main stem and then bending upwardly. Texture: Fine pubescence. Color: Close to 146C.

Leaf description:

*Arrangement.*—Alternate, simple.

*Length.*—About 3.5 cm.

*Width.*—About 3.4 cm.

*Shape.*—Palmately-lobed; roughly ovate with three to five lobes.

*Apex.*—Broadly acuminate.

*Base.*—Attenuate.

*Margin.*—Slightly dentate and palmately lobed; sinuses between lateral lobes divergent.

*Texture, upper and lower surfaces.*—Fine pubescence; slightly rough; veins prominent on lower surface.

*Color.*—Developing leaves, upper surface: Close to 137A. Developing leaves, lower surface: Close to 146B. Fully expanded leaves, upper surface: Close to 137B; venation, close to 144A. Fully expanded leaves, lower surface: Close to 147B; venation, close to 144B.

*Petioles.*—Length: About 1 cm. Diameter: About 2 mm. Texture, upper surface: Fine pubescence; slightly rough. Texture, lower surface: Fine pubescence. Color, upper surface: Close to 144A. Color, lower surface: Close to 144B.

Inflorescence description:

*Form and flowering habit.*—Decorative-type inflorescence form with ligulate-shaped ray florets; inflorescences borne on terminals above and beyond the foliar plane; disc and ray florets arranged acropetally on a capitulum; freely flowering habit with about 54 inflorescences developing per plant.

*Fragrance.*—Mildly fragrant; pungent, herbaceous.

*Flowering response.*—Early to mid-season flowering habit, plants exposed to natural season conditions begin flowering in late August to early September in the United Kingdom; plants flower uniformly and continuously.

*Inflorescence longevity.*—Inflorescences maintain good color and substance for about three to five weeks on the plant; inflorescences persistent.

*Inflorescence buds.*—Height: About 3 mm. Diameter: About 5 mm. Shape: Oblate. Color: Close to 138A.

*Inflorescence diameter*.—About 4.5 cm.

*Inflorescence height*.—About 1.6 cm.

*Receptacles*.—Height: About 3 mm. Diameter: About 3 mm. Shape: Conical. Color: Close to 139D.

*Ray florets*.—Number of ray florets per inflorescence: About 182 arranged in about eleven whorls. Orientation: Initially upright, then about 90° from vertical. Length: About 1.7 cm. Width: About 5 mm. Shape: Ligulate. Apex: Acute. Base: Fused into a short tube. Margin: Entire. Texture, upper and lower surfaces: Smooth, glabrous; double-keeled. Color: When opening, upper surface: Close to NN155B. When opening, lower surface: Close to NN155C. Fully opened, upper and lower surfaces: Close to NN155B; with development, color becoming closer to NN155C.

*Disc florets*.—Disc floret development has not been observed on plants of the new *Chrysanthemum*.

*Phyllaries*.—Number of phyllaries per inflorescence: About 24 arranged in about three whorls. Length: About 6 mm. Width: About 3 mm. Shape: Ovate. Apex: Obtuse. Base: Obtuse. Margin: Entire. Texture, upper surface: Smooth, glabrous; waxy. Texture, lower surface: Fine pubescence; waxy. Color, upper surface: Close to 146A. Color, lower surface: Close to 146B.

*Peduncles*.—Length, terminal peduncle: About 2.5 cm. Diameter, terminal peduncle: About 2 mm. Angle: About 10° from vertical. Strength: Moderately strong; flexible. Texture: Fine pubescence. Color: Close to 138B.

*Reproductive organs*.—Androecium: None observed. Gynoecium: Present only on ray florets. Pistil length: About 5 mm. Stigma shape: Bi-parted. Stigma color: Close to 12A. Style length: About 3 mm. Style color: Close to 8B. Ovary color: Close to NN155C.

*Seeds and fruits*.—Seed and fruit production has not been observed on plants of the new *Chrysanthemum*.

Disease & pest resistance: Resistance to pathogens and pests common to *Chrysanthemum* plants has not been observed on plants of the new *Chrysanthemum*.

Garden performance: Plants of the new *Chrysanthemum* have demonstrated good garden performance and to tolerate temperatures from about 0° C. to about 35° C.

It is claimed:

1. A new and distinct *Chrysanthemum* plant named 'Fidcsunwhi' as illustrated and described.

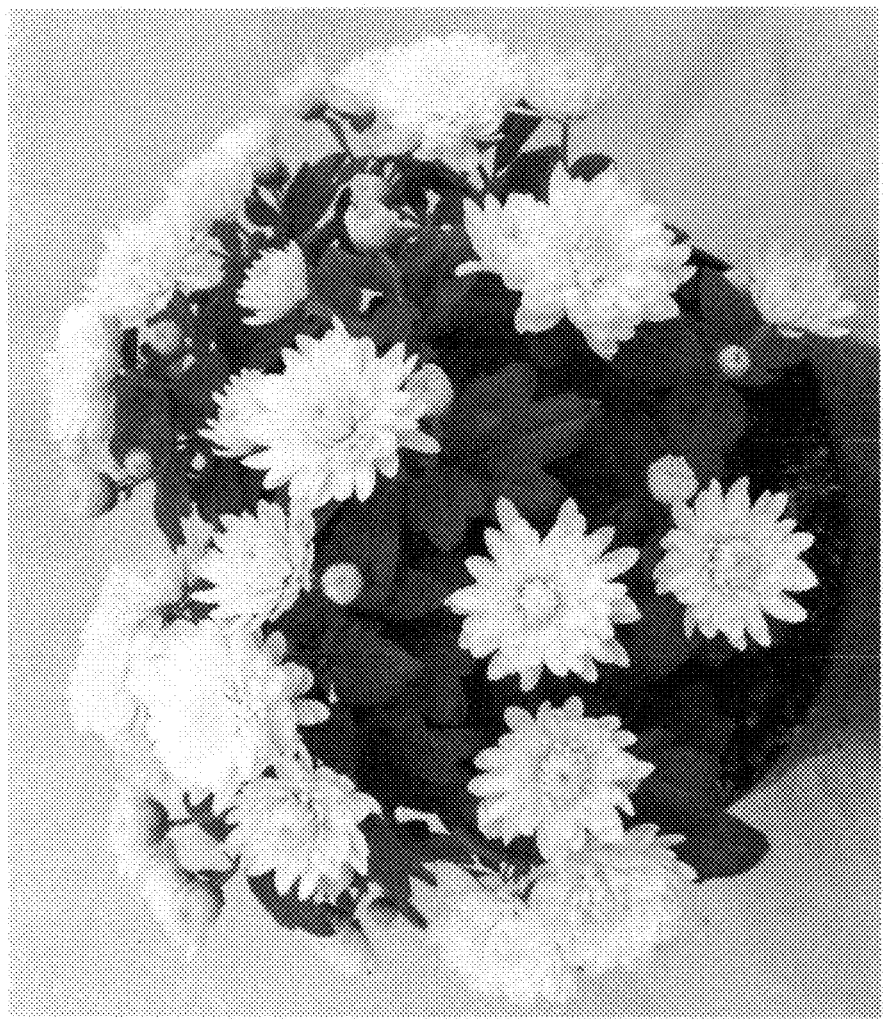

* * * * *